United States Patent
Saruwarati et al.

(10) Patent No.: US 7,008,387 B2
(45) Date of Patent: Mar. 7, 2006

(54) PORTABLE DEVICE FOR COLLECTING INFORMATION ABOUT LIVING BODY

(75) Inventors: Tomozumi Saruwarati, Chiba (JP); Hiroshi Odagiri, Chiba (JP); Yoshiharu Yamamoto, Tokyo (JP); Benjamin H. Natelson, New Brunswick, NJ (US)

(73) Assignees: Seiko Instruments Inc., Chiba (JP); University of Medicine and Dentistry of New Jersey, New Brunswick, NJ (US)

( * ) Notice: Subject to any disclaimer, the term of this patent is extended or adjusted under 35 U.S.C. 154(b) by 284 days.

(21) Appl. No.: 10/205,913

(22) Filed: Jul. 26, 2002

(65) Prior Publication Data

US 2003/0216671 A1    Nov. 20, 2003

(30) Foreign Application Priority Data

May 16, 2002 (JP) .............................. 2002-141917

(51) Int. Cl.
  *A61B 5/103* (2006.01)
  *A61B 5/117* (2006.01)
(52) U.S. Cl. ..................................................... 600/595
(58) Field of Classification Search ................ 600/595, 600/300, 301, 322, 481, 485, 544, 549, 561; 434/236, 365; 273/273, 460; 340/573.1, 340/384.73, 691.8; 310/321; 387/345, 395; 702/70; 345/501; 714/724, 736
See application file for complete search history.

(56) References Cited

U.S. PATENT DOCUMENTS

| | | | | |
|---|---|---|---|---|
| 4,770,636 A | * | 9/1988 | Buschke ...................... | 434/236 |
| 5,317,305 A | * | 5/1994 | Campman ................ | 340/573.1 |
| 6,126,595 A | * | 10/2000 | Amano et al. .............. | 600/300 |
| 6,327,544 B1 | * | 12/2001 | Samuels ...................... | 702/70 |
| 6,485,417 B1 | * | 11/2002 | Bowles et al. .............. | 600/300 |

* cited by examiner

*Primary Examiner*—Max F. Hindenburg
*Assistant Examiner*—Brian Szmal
(74) *Attorney, Agent, or Firm*—Adams & Wilks

(57) ABSTRACT

A portable device for collecting information about a human body is adapted to be worn on the human body and is capable of periodically performing cognitive faculty tests during daily life to discern fluctuations in the memory faculty of a wearer. The device displays a problem of cognitive tests on a display unit, and a wearer inputs an answer with an input unit. The wearer's response time is clocked with a clock unit, and the answer and the response time are stored in a memory unit in time sequence by control of a control circuit. The device can include a detection unit for detecting a living body signal to enable research on the relationship between behavioral patterns or temperamental trends and memory faculties, and the like.

12 Claims, 10 Drawing Sheets

PORTABLE DEVICE FOR COLLECTING INFORMATION ABOUT LIVING BODY

BACKGROUND OF THE INVENTION

1. Field of the Invention

The present invention relates to a portable device for collecting, in time sequence, information about the living body of a wearer of the device in his or her daily life.

2. Description of the Related Art

It is widely known that conventional living body information monitoring devices are used to continuously measure living body information to assist in health care, diagnosis and treatment. For example, step counters and the like are in widespread use, and count the number of steps made by a wearer in walking to determine the amount of exercise done by the wearer. In use of such step counters, measurement is continuously performed and measurement data is handled by being totalized, where the total number of steps in one day is used as an index for health care.

A U.S. Pat. No. 5,197,489 discloses an attempt to record bodily movements of a wearer in time sequence to use the recorded data in treatment and/or diagnosis.

By combining such living body information monitoring devices with pulse sensors and temperature in addition to measurement of changes in his or her bodily movements and in the amount of activity, it becomes possible to perform objective recording of such information in time sequence. However, the present applicant has pointed out a problem that these devices cannot obtain subjective information relating to causes, such as why the wearer was active, nor mental information such as how the wearer felt at the time. Thus, the applicant has proposed a portable device for collecting information about a living body, capable of periodically obtaining subjective information about the wearer as well.

On the other hand, the latest research is beginning to show interest in the relationship between cognitive faculty tests, which are used to diagnose Alzheimer's Disease and senile dementia, and behavioral patterns, and the relationship between the cognitive faculty tests and temperamental trends. Such cognitive faculty tests include several varieties such as immediate free repetition exercises in which 15 simple words such as "barley tea" or "mackerel" are shown consecutively on a computer screen at 3-second intervals, and then the patient responds by repeating these after 90 seconds; delayed confirmation exercises in which the patient responds by repeating the first 15 words of 30 words comprised of 15 new words added to the previous 15 words; and immediate confirmation exercises in which freely selected characters are displayed at random and the patient is asked whether characters that are displayed successively in time sequence were the same character or not, and so on. However, all of the tests evaluate the short-term memory faculty, and examine the function of the frontal lobe portion of the brain which governs this part. These tests are commonly called frontal lobe function tests, or cognitive faculty tests. Further, each of these tests (hereinafter, referred to as "cognitive faculty tests" in this specification) is performed using a computer at a hospital or a clinic.

Since the conventional cognitive faculty tests were performed using the hospital or clinic computer, they could not grasp subtle fluctuations in the memory faculty of the patient in his or her daily life.

SUMMARY OF THE INVENTION

An object of the present invention is to provide a portable device for collecting information about a living body, capable of periodically performing a cognitive faculty test during daily life to thereby grasp fluctuations in the memory faculty, and capable of being worn on the human body. A further object is to provide a portable device for collecting information about a living body for use in the latest research on the relationship between behavioral patterns and the memory faculty, and the relationship between temperamental trends and the memory faculty.

The cognitive faculty test in the present invention is of the immediate-confirmation-exercise type, due to the characteristics of the portable device for collecting information about a living body. That is, the format of the questions is such that the answer thereto can be given with a single operation, as in "correct or incorrect?", "more than or less than?", "left or right?", and "up or down?".

The portable device for collecting information about a living body according to the present invention is composed of: storage means for storing a plurality of characters; character selection means for selecting a character from the storage means; display means for displaying the selected character; input means for inputting information about the character displayed in the display means; measuring means for clocking time from the display of the character until the input; and memory means for storing the information inputted with the input means and the time measured by the measuring means.

Further, it is assumed that the portable device for collecting information about a living body according to the present invention will be used in daily life. Thus, the device further comprises delaying means for delaying answering a question. In situations where the wearer cannot answer, such as when running hurriedly, and during meetings and so on, when the wearer performs an input indicating that he or she cannot answer, the delaying means starts the question again, for example, 30 minutes later. Since the device has this delayed questioning function, the collecting of information can be performed without disrupting daily life.

DETAILED DESCRIPTION OF THE PREFERRED EMBODIMENTS

Hereinafter, an embodiment of the present invention is explained with reference to the drawings.

Figure 1A:
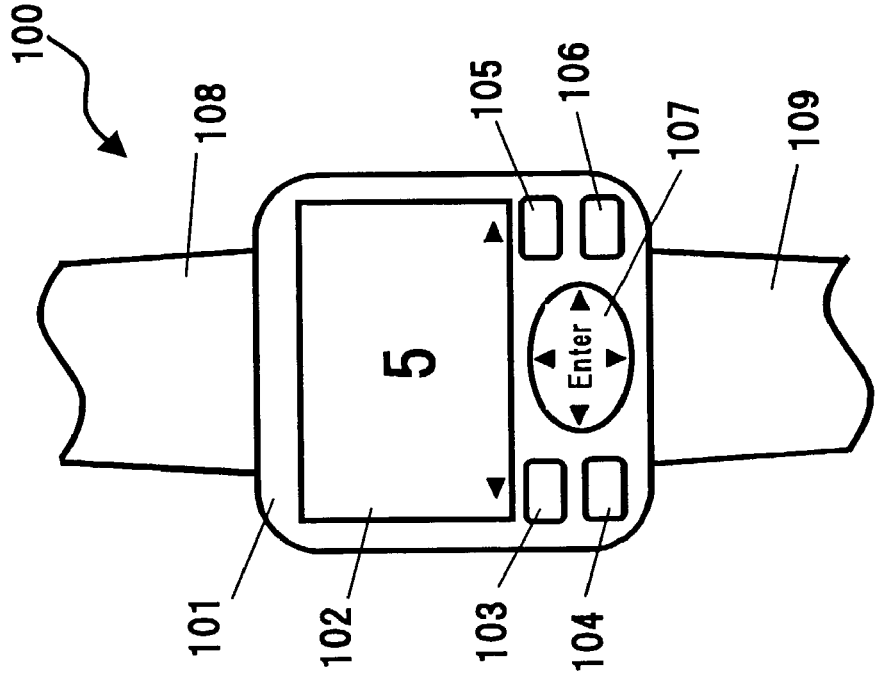
FIGS. 1A and 1B are views showing an appearance of a portable device for collecting information about a living body according to an embodiment of the present invention.
Figure 1B:
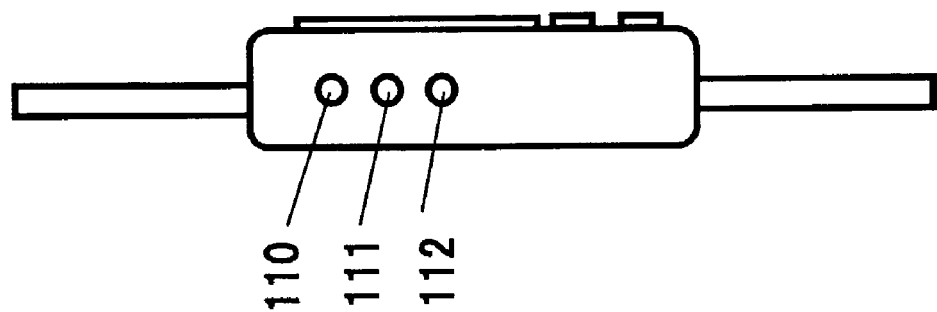

FIGS. 1A and 1B are views showing an appearance of a portable device for collecting information about a living body according to an embodiment of the present invention, where FIG. 1A is a plan view and FIG. 1B is a side view. A portable device for collecting information about a living body 100 is composed of a main unit 101 and a pair of bands 108 and 109, and can be worn on the wrist of a wearer by means of the bands 108 and 109. The main unit 101 has a display portion 102 and a plurality of keys 103, 104, 105, 106 and 107. The display portion 102 is, for example, an LCD or other such display device, and it usually displays the time of day so that the present portable device for collecting information about a living body 100 may be used as a wristwatch with a clock function. When a cognitive faculty test is performed, freely selected characters repeatedly appear and disappear again and again in the display portion 102. The wearer judges the chronical relationship between the characters and inputs the result using the key 107.

In the present embodiment, the key 107 is a cursor-key type input device with 4 axes of up, down, left and right, which is thoughtfully arranged such that, for example, when testing whether characters which are displayed successively in time sequence are mutually identical or not identical, a simple manipulation may be used in which right indicates "identical", and left indicates "not identical", so that the wearer can concentrate only on remembering. The other keys 103, 104, 105 and 106 are used to realize other functions, such as switching modes, correcting the time and the like. Explanations of these are omitted since they are not directly related to the present invention. Since the portable device for collecting information about a living body of the present invention is constructed as a wristwatch, when the cognitive faculty tests are not being performed, it is convenient for the wearer if the display portion 102 shows the time of day. A side surface of the main unit 101 is formed with input/output terminals 110, 111 and 112 for use with an external personal computer or the like.

Figure 2:
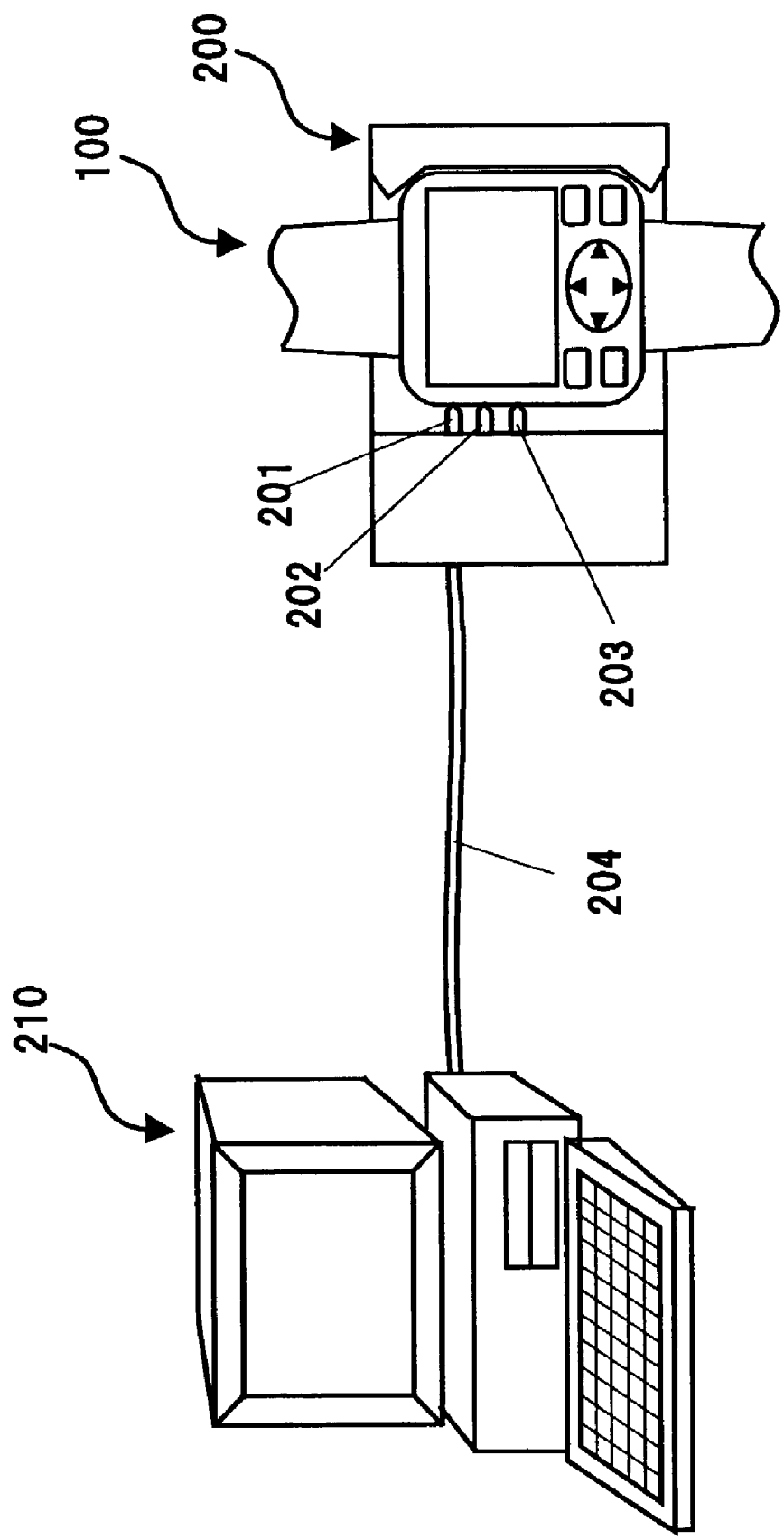
FIG. 2 is a schematic drawing showing a state where the portable device for collecting information about a living body and a personal computer are connected to each other and communication is performed therebetween.

FIG. 2 is a schematic view showing a state where the portable device for collecting information about a living body 100 and a personal computer (hereinafter referred to as the "PC") 210 are connected to each other and communication is performed therebetween.

The portable device for collecting information about a living body 100 is connected to the PC 210 through a docking station 200. The docking station 200 is provided with connection pins 201, 202 and 203, and the connection pins 201, 202 and 203 can be brought into contact with the input/output terminals 110, 111 and 112, respectively, of the portable device for collecting information about a living body 100, and are connected to an input/output port of the PC 210 by a cable 204. By performing communication between the portable device for collecting information about a living body 100 and the PC 210, results of the cognitive faculty tests can be transferred easily to the PC 210.

The PC 210 uses various analytical software to analyze the test results which have been sent to it. By performing the communication between the portable device for collecting information about a living body 100 and the PC 210, various data about settings for the living body information detection and questions prepared for evaluating the temperamental trends and the like also can be written easily from the PC 210 to the portable device for collecting information about a living body 100.

In FIG. 2, the docking station 200 and the cable 204 are used for the connection between the PC 210 and the portable device for collecting information about a living body 100; however, infrared or other such communications means may be used without using the station or the cable.

Figure 3:
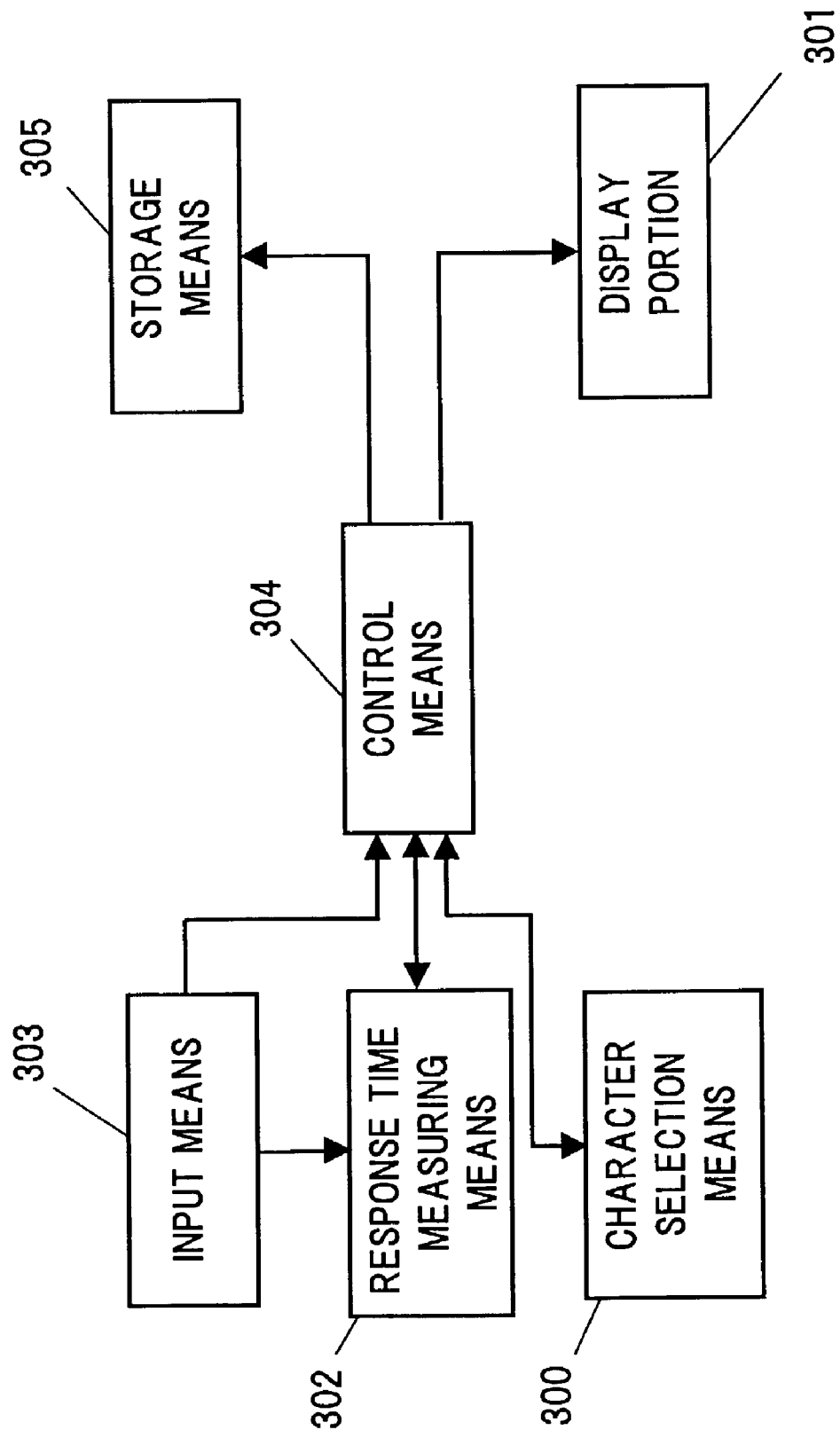
FIG. 3 is a diagram showing the configuration of the portable device for collecting information about a living body of the present invention.

FIG. 3 is a diagram showing the configuration of the portable device for collecting information about a living body 100.

A control means 304 executes the cognitive faculty tests at predetermined time intervals. When a cognitive faculty test is started, first, the control means 304 causes character selection means 300 to randomly select one character from among plural kinds of characters as a first character. The control means 304 causes a display portion 301 to display the selected first character for a given duration of time.

The display portion 301 corresponds to the display portion 102 shown in FIG. 1. After the control means 304 has caused the first character to be displayed in the display portion 301 for the given duration of time, it turns the first character off and causes the character selection means 300 to randomly select a second character from the plural kinds of characters, similarly to the first character. When the second character is displayed in the display portion 301 similarly to the first character, the control means 304 simultaneously causes response time measuring means 302 to start measuring.

The wearer of the portable device for collecting information about a living body of the present invention uses an input means 303 to answer with information about the characters, such as how the first character and the second character displayed in time sequence were related to each other, for example whether they were the same, or whether they were different from each other. This input means 303 corresponds to the key 107 shown in FIG. 1.

When there is an input from the input means 303, the response time measuring means 302 immediately stops measuring time. The measuring of the response time is performed when showing the characters on the even-number-times (when showing the 2nd character, 4th character, 6th character, etc.). The control means 304 causes memory means 305 to store the information about whether or not the input from the input means 303 was correct, and the time measured by the response time measuring means 302. After the control means 304 causes the storage means 305 to store the correct/incorrect information and the measured time, it resets the response time measuring means 302 and causes the character selection means 300 to randomly select a third character from the plural kinds of characters once again. The cognitive faculty test is executed by repeatedly performing, for a given duration of time, the above-mentioned operation, from the selection of the first character to the resetting of the response time measuring means 302 by the control means 304.

Figure 4:
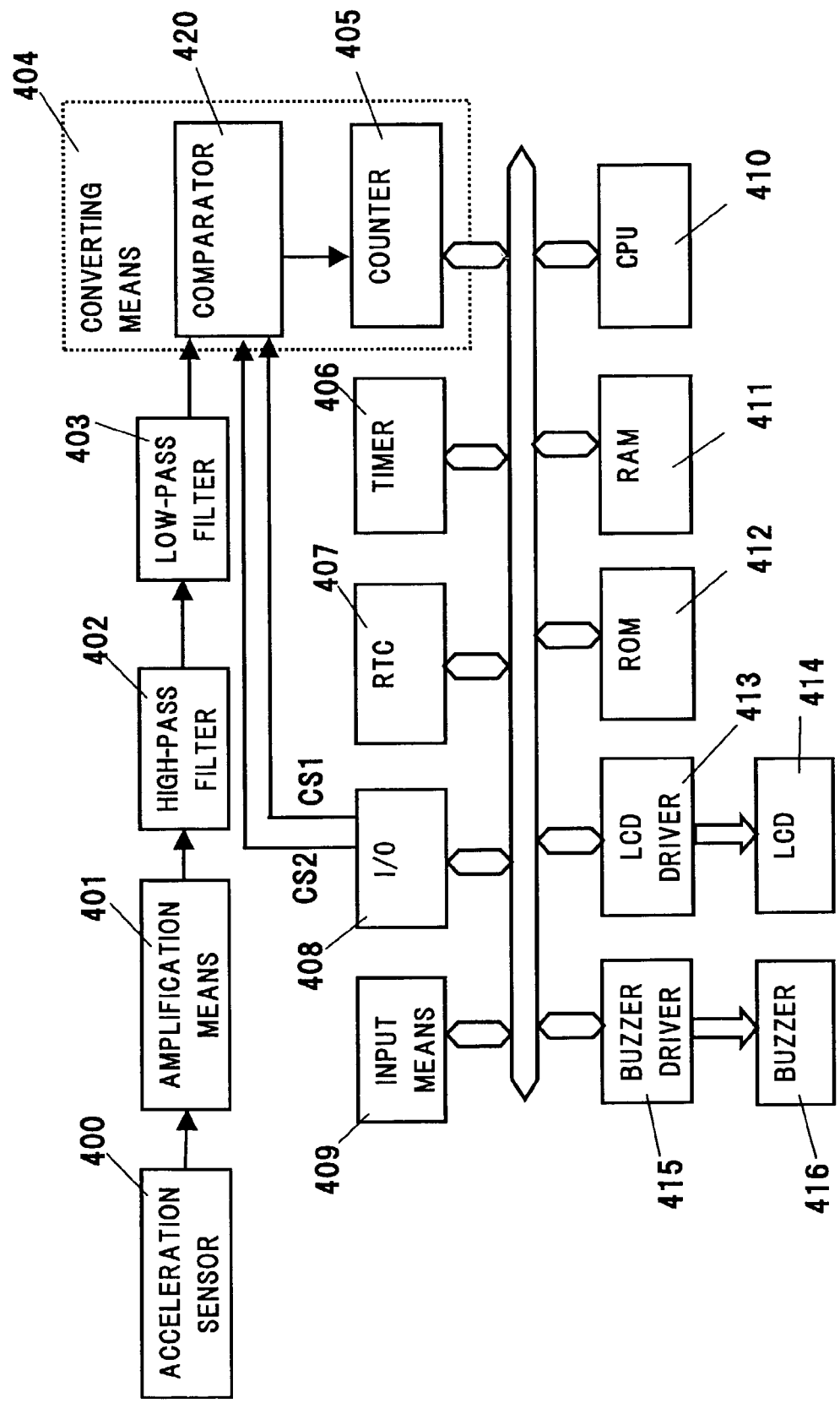
FIG. 4 is a block diagram showing an embodiment of the present invention.

FIG. 4 is a block diagram showing an embodiment of the present invention. An input means 409, an I/O port 408, a real time clock (hereinafter referred to as the "RTC") 407, a timer 406, a buzzer driver 415, an LCD driver 413, a ROM 412, a RAM 411 and a CPU 410 are connected to a bus line.

An output from the buzzer driver 415 is connected to a buzzer 416, an output from the LCD driver 413 is connected to an LCD 414. The cognitive faculty tests can be realized with the above-mentioned construction, but in FIG. 4, a construction enabling behavior patterns of the wearer to be recorded is added as well as one of the living body information.

An acceleration sensor 400 is a piezoelectric-type acceleration sensor having a piezoelectric element made of lithium niobate, lead ziconate-titanate or the like formed as a cantilever. The piezoelectric element bends with acceleration to generate an electric charge. That is, the acceleration sensor 400 detects acceleration according to a movement of the wearer and outputs a signal.

The signal is amplified by an amplification means 401. Since the amplified signal includes various noises and high-frequency components, only necessary frequency components are extracted from the signal by a high-pass filter 402 and a low-pass filter 403. The signal extracted by the high-pass filter 402 and the low-pass filter 403 and representing bodily movements of the wearer is quantified and converted into a numeric value by converting means 404.

Methods of converting the signal representing the bodily movements into a numeric value include a method of performing direct A/D conversion of the signal, and a method of digitizing it by comparison with a reference voltage. The latter method is preferable in terms of reduction in size and in power consumption. In this embodiment, therefore, the conversion means is arranged to digitize the bodily movement signal. A reference voltage used by a comparator 420 is set by signals CS1 and CS2 from an I/O port 408. The comparator 420 compares the reference voltage and the bodily movement signal to convert the analog bodily movement signal into a binary digital signal. The converted digital signal is inputted to a counter 405 to be converted into a numeric value.

Figure 5:
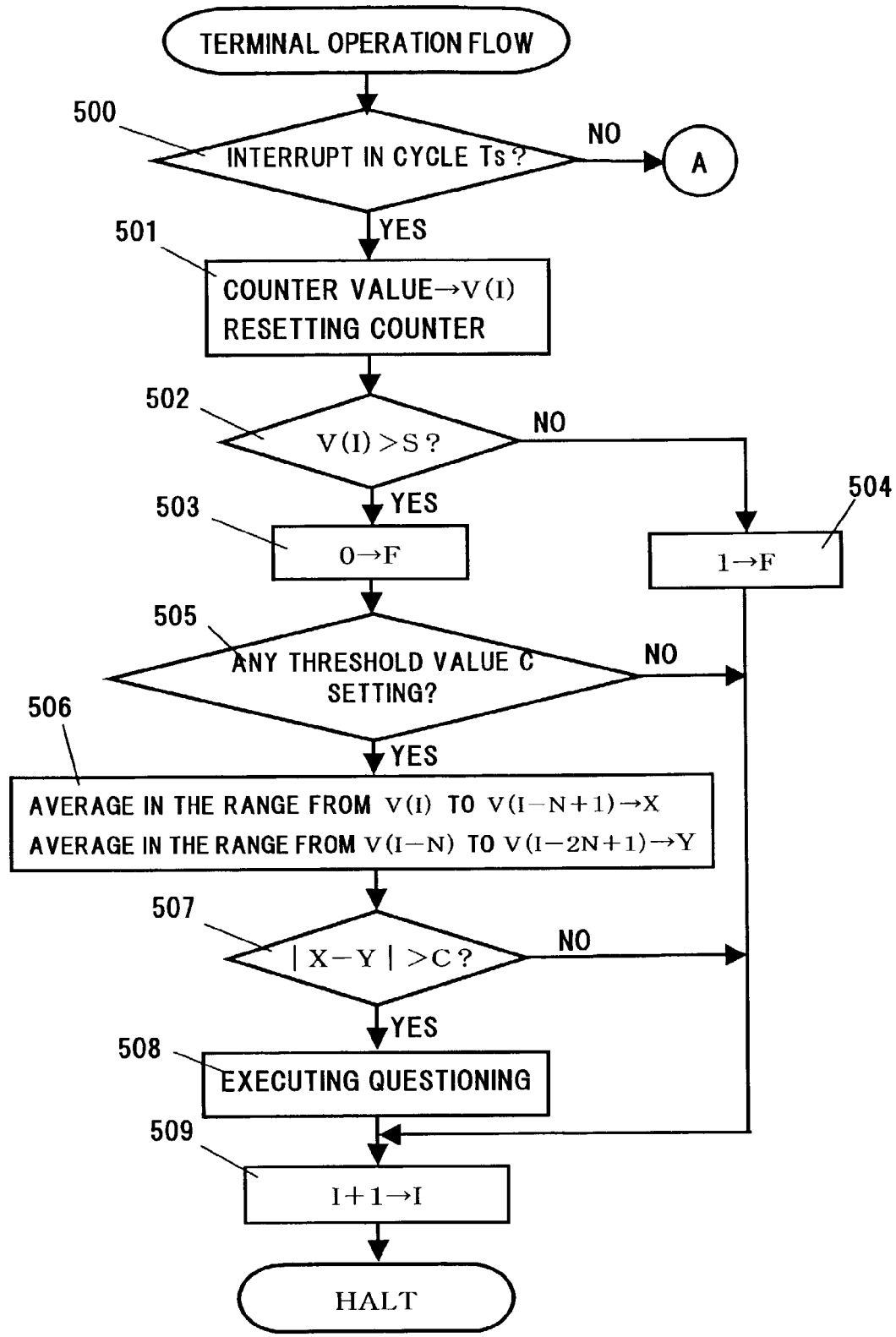
FIG. 5 is a diagram showing a flow of operations of a cognitive faculty test according to the present invention.

A flow of operations in the cognitive faculty test is shown in FIG. 5, and these operations are explained together with FIG. 4.

The timer 406 generates an interruption in each bodily movement detection cycle Ts and in each cognitive faculty test execution cycle Tc which are set in advance. When an interruption occurs, the CPU 410 begins processing according to a processing program stored in the ROM 412. When the interruption is not a Tcn interruption a different processing is executed; and when the interruption is the Tcn interruption the cognitive faculty test is started (process 500).

First, the starting of the cognitive faculty test is notified to the wearer by sounding the buzzer (process 501). Then, a count value I indicating the number of operation times is reset (process 502). Next, measuring performed by a test-time-measuring timer for managing the execution time of the cognitive faculty test is started (process 503).

As one specific example, the time information in the RTC 407 is read out and a test finish time calculated by adding the test time thereto is stored in the RAM 411. Next, the CPU 410 generates a rectangular distribution random number and stores the random number in the RAM 411 (process 504). Next, the CPU 410 selects the first character corresponding to the random number, and displays it on the LCD 414 via the LCD driver 413 (process 505).

Here, if the random number generated at process 504 is an integer, the random number may be immediately displayed on the LCD 414. The CPU 410 turns off the displayed character after 1 second (process 506).

Next, the CPU 410 generates a rectangular distribution random number again and stores the random number in the RAM 411 (process 507). Next, the CPU 410 selects the second character corresponding to the random number, and displays the second character on the LCD 414 via the LCD driver 413 (process 508). Next, the CPU 410 approves a relatively fast timer interruption, for example, 64 Hz interruption, and causes the response-time timer to start clocking by having the RAM 411 count the 64 Hz interruption (process 809). After starting the response-time timer at process 809, the CPU 410 waits for a switch input from the wearer in a waiting-for-switch-input state (process 510).

In a case where there is no switch input from the wearer after 1 second, the second character is turned off from the screen (processes 516 and 517). In a case where there is no switch input from the wearer after 5 seconds, the CPU 410 stores the count value I indicating the number of operation times into an array K(I) in the RAM 411, and, likewise, a "2" indicating that there was no response within 5 seconds into an array A(I), and clocking value Rt from the response-time timer into an array T(I), and then the CPU 410 exits the waiting-for-switch-input state.

In a case where there was a switch input from the wearer within 5 seconds after the display of the second character, the clocking by the response-time timer is immediately stopped (process 511). Further, if the second character is being shown on the LCD 414, this is turned off as well (process 512). The results which the wearer inputted with the input means 409 are evaluated at process 513.

In the case where the random number stored in the RAM at the time when the first character was selected, and the random number at the time when the second character was selected, are the same, if the wearer used the input means 409 to perform the input meaning that the characters were the same, the CPU 410 stores the count value I indicating the number of operation times into the array K(I) inside the RAM 411, and stores a "1" indicating that the wearer's answer was correct into the array A(I), and stores the clocking value Rt of the response-time timer into the array T(I), and then the CPU 410 exits the waiting-for-switch-input state.

In the case where the random number stored in the RAM at the time when the first character was selected, and the random number at the time when the second character was selected, are the same, but the wearer used the input means 409 to perform an input meaning that the characters were "different", or in a case where the random number stored in the RAM at the time when the first character was selected and the random number at the time when the second character was selected are different, but the wearer used the input means 409 to perform the input meaning "same", the CPU 410 stores a "0" meaning that the wearer's answer was wrong into the array A(I), and stores the clocking value Rt of the response-time timer into the array T(I), and then exits the waiting-for-switch-input state.

When the CPU 410 exits the waiting-for-switch-input state, the response-time timer is reset, and the 64 Hz interruption is prohibited. Next, at process 521, it is confirmed whether or not the test time has elapsed. As long as the test time has not yet finished, the test returns to process 503 again to display the next character, and repeats the processing from the display of the first character (process 505) to the resetting of the response-time timer (process 521). In the case where the test time has already elapsed, the cognitive faculty test ends at "HALT" (process 522). According to the construction and operations described above, the portable device for collecting information about a living body can execute a cognitive faculty test.

The embodiment of the present invention shown in FIG. 4 is configured such that bodily movements of the wearer also can be collected as living body information.

Figure 6:
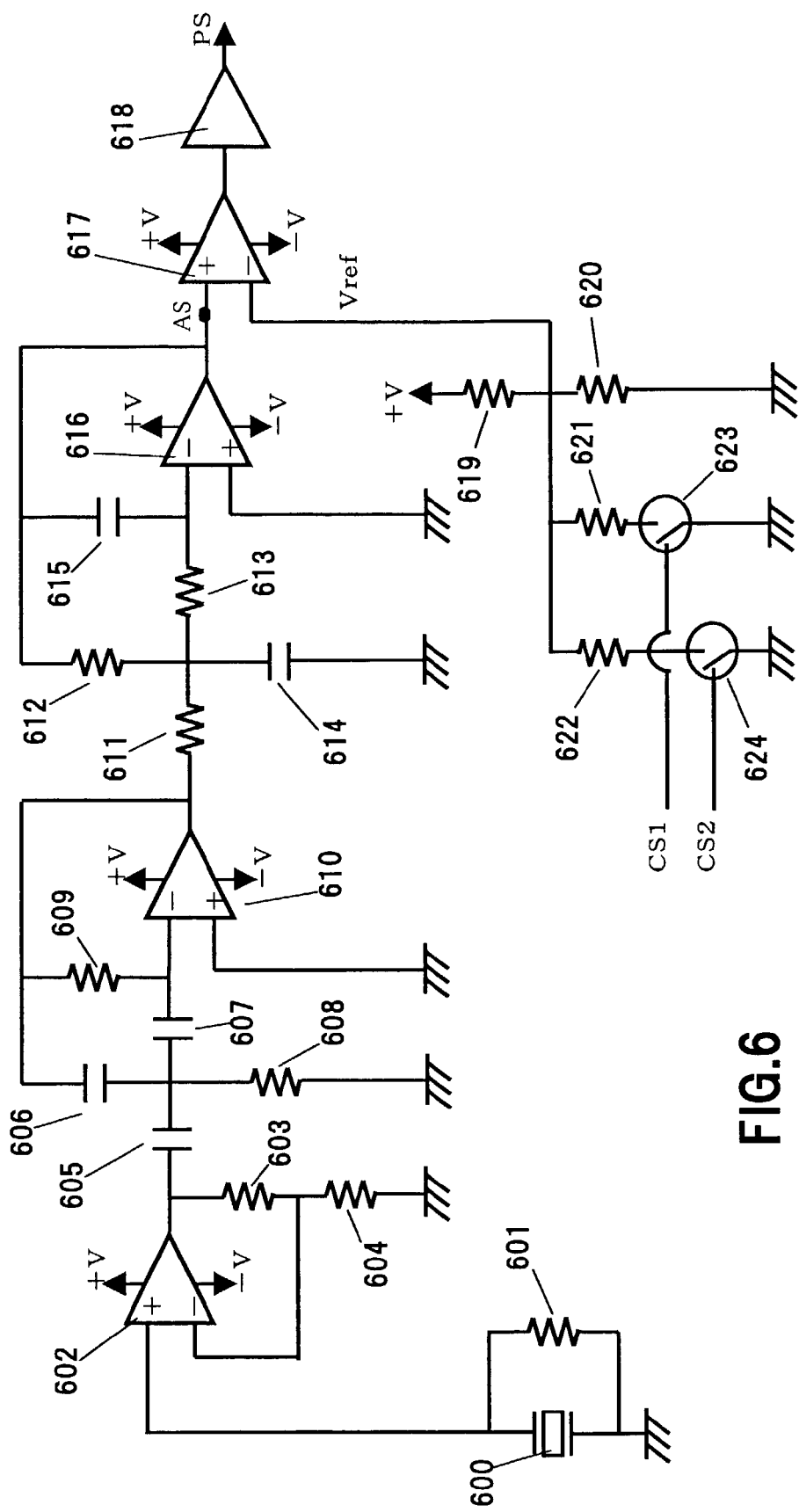
FIG. 6 is a diagram showing a specific example of a bodily movement detection circuit according to the present invention.

FIG. 6 illustrates a specific example of a bodily movements detection circuit, and operations thereof will now be explained. A piezoelectric-type acceleration sensor 600 is connected in parallel to a resistor 601, and one end of the sensor 600 is grounded. The other end of the sensor 600 is an output terminal which generates a voltage that is proportional to the acceleration. This output terminal connects to anon-inverting input terminal of an operational amplifier 602. The inverting input terminal of the operational amplifier 602 is connected to the output terminal of the operational amplifier 602 via a feedback resistor 603, and to the ground via a resistor 604, whereby it constitutes an amplifier circuit as a whole. The output terminal of the operational amplifier 602 is further connected to an inverting input terminal of an operational amplifier 610 via condensers 605 and 607.

An output terminal of the operational amplifier 610 constitutes a feedback circuit due to operation of a feedback resistor 609 and a condenser 606. A contact point of the condensers 605, 606 and 607 then is grounded via a resistor 608. The operational amplifier 610 and the condensers 605, 606 and 607 and the resistors 608 and 609 constitute a multi-feedback-type high-pass filter.

An output terminal of the operational amplifier 610 connects to an inverting input terminal of a subsequent operational amplifier 616 via resistors 611 and 613. An output terminal from the operational amplifier 616 constitutes a feedback circuit together with a feedback resistor 612 and a condenser 615. Further, a contact point of the resistors 611, 612 and 613 is grounded via a condenser 614.

The operational amplifier 616, the resistors 611, 612 and 613, and the condensers 614 and 615 constitute a multi-feedback-type low-pass filter. An output from the operational amplifier 616 connects to a non-inverting input terminal of an operational amplifier 617. Further, a reference voltage Vref is supplied to an inverting input terminal of the operational amplifier 617, so that the operational amplifier 617 operates as a comparator. The reference voltage Vref is generated by means of resistors 619, 620, 621 and 622 and analog switches 623 and 624. The analog switches 623 and 624 are turned ON and OFF by signals CS1 and CS2, respectively, to change the value of the reference voltage Vref and to change the sensitivity of the operational amplifier 617. The outputs from the operational amplifier 617 are formed into rectangular waves of a partial power source by means of a buffer 618. The rectangular waves are inputted into the counter 405, which is shown in FIG. 4, where the waves are counted.

Figure 7:
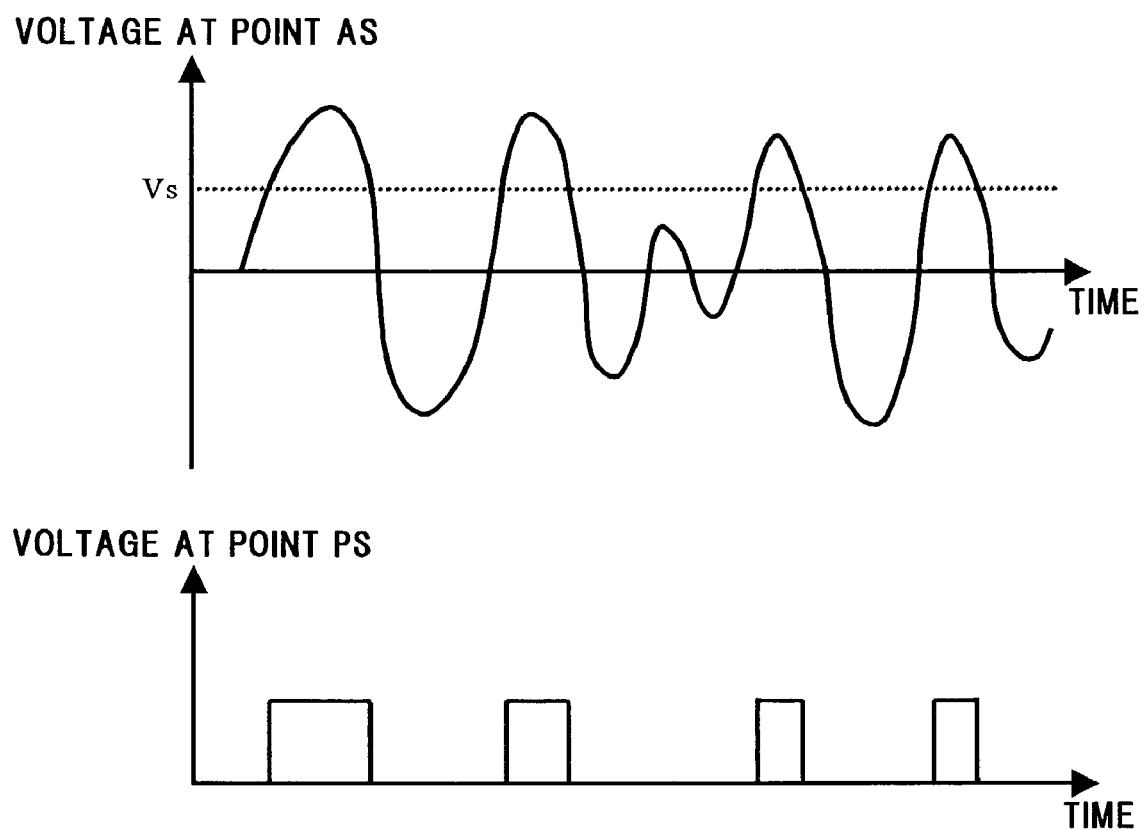
FIG. 7 is a diagram showing a waveform of an output from the bodily movement detection circuit of the portable device for collecting information about a living body according to an embodiment of the present invention.

FIG. 7 illustrates waveforms at an AS point and of an output PS shown in FIG. 6.

At the AS point, an analog signal expressing the bodily movements of the wearer is inputted, and this signal is compared with the reference voltage Vref by means of the comparator. The output from the comparator is shaped by the buffer such that its waveform at the PS point is that of a binary rectangular wave.

Figure 8:
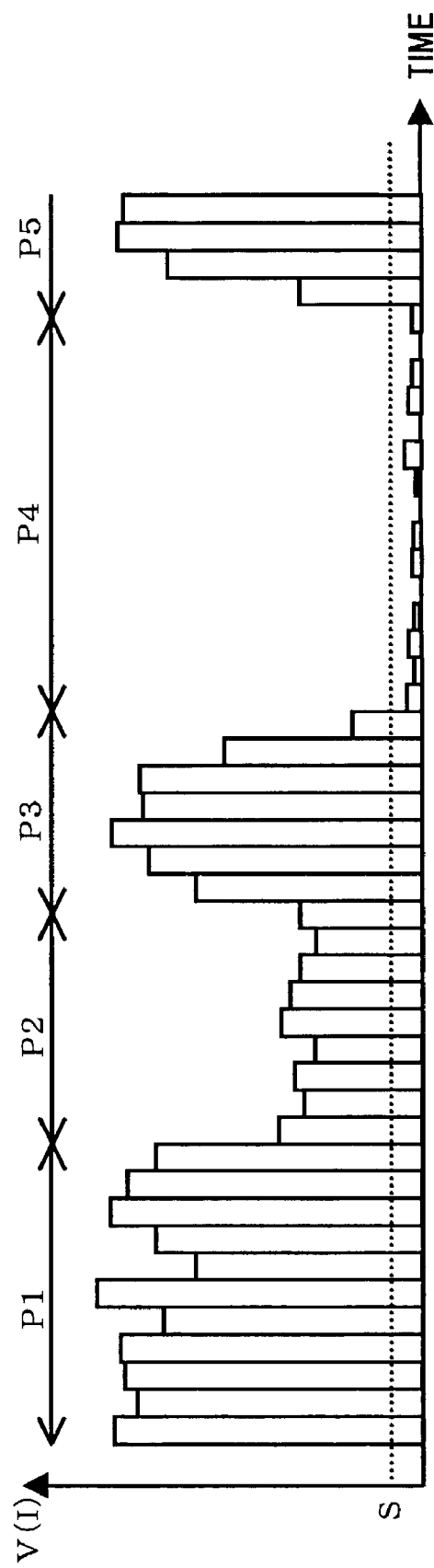
FIG. 8 is a graph showing the results of measurements with the portable device for collecting information about a living body according to the embodiment of the present invention.

The rectangular wave is generated with the bodily movements of the wearer, and it is accumulated in the counter 405 and initialized when it is read out with each bodily movements detection cycle Ts. Therefore, the count value generated with the bodily movements of the wearer during the bodily movements detection cycle Ts is recorded into the RAM. FIG. 8 illustrates an example of a case where measuring results are uploaded to a PC and turned into a graph after the measuring of the bodily movements has ended. The horizontal axis of FIG. 8 indicates time, and the vertical axis indicates the count value representing the bodily movements. As shown in FIG. 8, the wearer's activity of 1 day is clearly manifested. The activity of the day can be confirmed, that is, before noontime (period P1) the activity is lively, then becomes slightly inert after noontime, then active again before going to sleep (period P3), and then in period P4 the wearer is sleeping.

As described above, using the portable device for collecting information about a living body according to the present invention, the activity of the wearer can be recorded easily. Since the periodic cognitive faculty tests can be carried out simultaneously as well, it is possible to learn the wearer's activity level in addition to the fluctuations in his or her memory faculty.

The operations of the cognitive faculty test explained using FIG. 5 were explained assuming that when the interruption Tc for starting the cognitive faculty test is generated, the test starts unconditionally. However, the portable device for collecting information about a living body according to the present invention is used in daily life, and there are many instances where it is impossible to respond to tests at prescribed, completely regular intervals. To overcome this problem, the present invention is provided with a test delay function.

Figure 9:
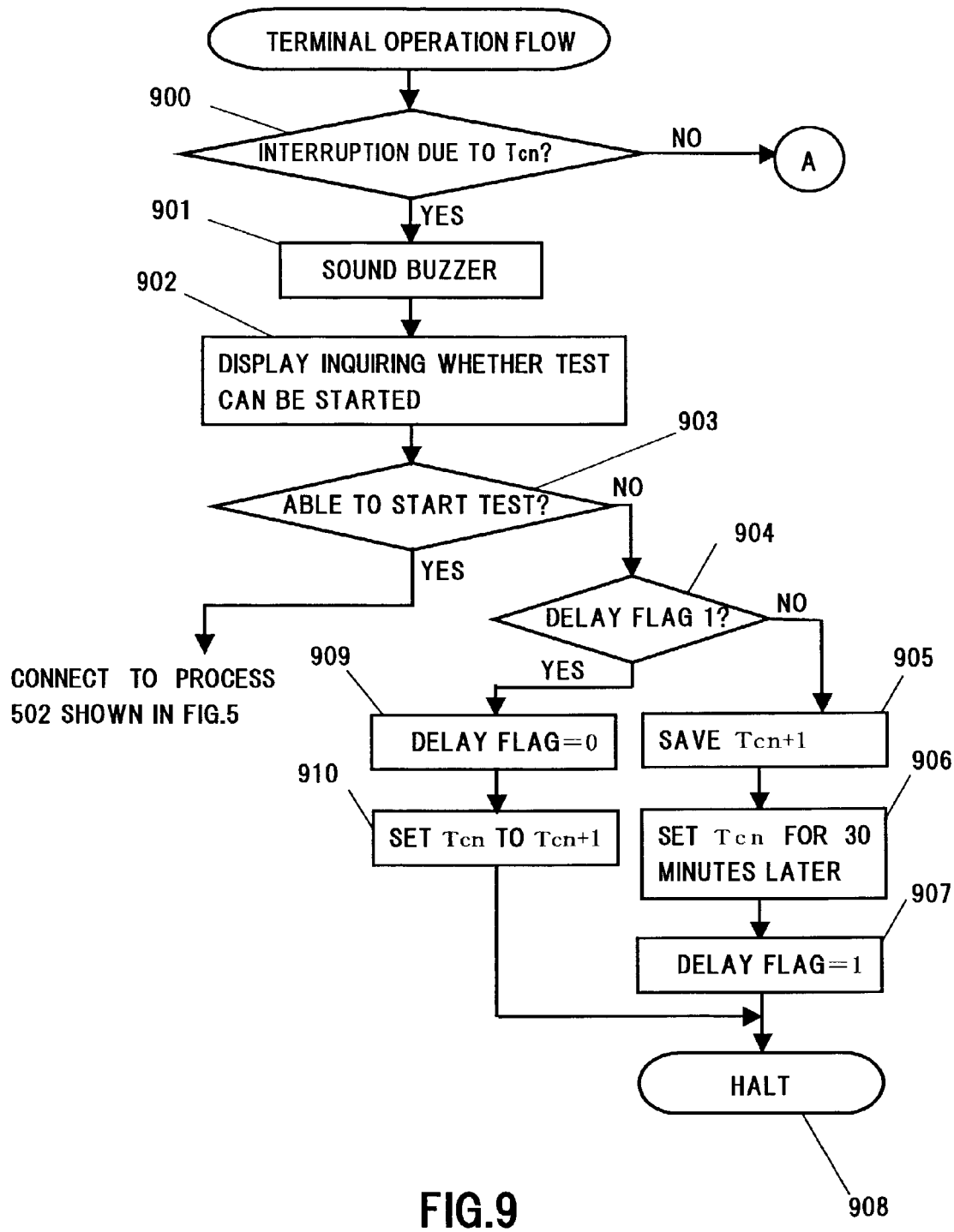
FIG. 9 is a flowchart of operations explaining processing for delaying the start of a test for a given amount of time according to the present invention.

In anticipation of times where the wearer cannot respond to the test for some reason when the interruption Tc at the start of the cognitive faculty test is generated, a display inquiring whether or not the wearer can respond to the test appears in the LCD at the time when the interruption Tc is generated. An operational flow of processing for delaying the start of the test for a given amount of time when the wearer cannot respond to the test is shown in FIG. 9, and operations thereof will now be explained.

At the time of the interruption generated at the execution time Tcn for the cognitive faculty test, the buzzer is sounded (process 901) to notify the wearer that the start time for the cognitive faculty test has arrived. Simultaneously, the display asking whether the test can be started is displayed on the LCD (process 902). If the test can be started, the processing at process 502 explained above and indicated in FIG. 5 is performed. If the test cannot be started, the operation transfers to a test start delay processing (process 903).

At process 904, it is verified whether or not a delay flag has been set to confirm whether or not the delay processing has already been performed. If the delay flag is 0 and the delay processing performed at this execution time Tcn is the first delay processing, the next test start time, that is, a test execution time Tcn+1, is temporarily saved into another area of a memory (process 905). Then, the next test start time is set for 30 minutes later (process 906). Then, the delay flag is set (process 907), and the operation is ended (process 908).

The above-mentioned processing enables one of the cognitive faculty tests, which are scheduled regularly, to be delayed for the given amount of time.

In a case where a delay flag has already been set at process 904, the current delay operation performed at the test execution time Tcn will be the second delay operation; therefore, in the present embodiment, the delay flag is reset (process 909), and the next test execution time Tcn+1 is set once again to the test start time that was temporarily saved at process 905 and the operation is ended (process 908). In other words, in the case of the present embodiment the delay operation is permitted only once; therefore, in the case where the delay operation is a second delay operation, the current test scheduled for the test execution time Tcn is cancelled, and the next test execution time is set once again to a regular time.

The test start time can be easily delayed as described above.

Note that, in accordance with the embodiment that was explained, if tests scheduled for Tcn+x continue to be repeated the wearer will be woken up during his or her sleep as well. One possible method to prevent this is to use the results of the bodily movement measurements to automatically detect that the wearer has gone to sleep and prohibit the starting of the cognitive faculty tests.

That is, as explained using FIG. 7, by viewing at the results of the bodily movement measurements, the portable device for collecting information about a living body can be used to detect whether or not the wearer is sleeping; therefore, sleep can be detected automatically, and the cognitive faculty tests can be prohibited. Further, instead of doing this automatically as described above, information pertaining to sleep and wake-up of the user may be inputted into the portable device for collecting information about a living body with an operation performed by the user, so that the cognitive faculty test is not performed while the wearer is sleeping.

As described above, in accordance with the present invention, the cognitive faculty test used in the diagnosis of Alzheimer's Disease and dementia can be performed with the portable device for collecting information about a living body, and moreover information about the activity of the wearer can be recorded as well, to thereby provide a portable device for collecting information about a living body for use in the latest research on the relationship between behavioral patterns and memory faculties, the relationship between temperamental trends and memory faculties and the like.

What is claimed is:

1. A portable device for collecting information about a user, comprising: a case mountable on the user's wrist; storage means disposed in the case for storing a plurality of characters; character selection means for selecting a character from the storage means; a display provided on the case for displaying the selected character; input means for allowing user input of information about the character displayed on the display; measuring means disposed in the case for measuring elapsed time from the display of the character until occurrence of the user input; memory means disposed in the case for storing the information input by the user and the time measured by the measuring means; control means for controlling operations of the character selecting means and the memory means control means for controlling operations of the character selecting means and the memory means, the control means having a timer, and, at predetermined time intervals measured by the timer, causing the memory means to store the information input by the user with the input means and the time measured by the measuring means; and delaying means for delaying the start of operation of the memory means to cause the memory means to store the information input by the user with the input means and the time measured by the measuring means at a different time delayed from the predetermined time intervals.

2. A portable device for collecting information about a living body according to claim 1; wherein the delaying means includes a switch mounted on the case.

3. A portable device for collecting information about a user according to claim 1; wherein the memory means stores the information input by the user with the input means and the time measured by the measuring means for a plurality of sets of sequentially displayed characters that are displayed in time sequence and for a given duration of time.

4. A portable device for collecting information about a user according to claim 1; wherein the input means comprises a cursor key mounted on the case.

5. A portable device for collecting information about a user according to claim 1; further comprising detection means for detecting bodily movements of the user.

6. A portable device for collecting information about a user according to claim 5; wherein the detection means is an acceleration sensor.

7. A portable device for collecting information about a user, comprising: a case mountable on the user's wrist; storage means disposed in the case for storing a plurality of characters; character selection means for sequentially selecting the plurality of characters from the storage means; a display provided on the case for sequentially displaying the selected plurality of characters; input means provided on the case for allowing user input of information about sequentially displayed characters; measuring means disposed in the case for measuring elapsed time from the display of the sequentially displayed characters until occurrence of the user input; memory means disposed in the case for storing the information input by the user and the time measured by the measuring means; control means for controlling operations of the character selecting means and the memory means, the control means having a timer, and, at predetermined time intervals measured by the timer, causing the memory means to store the information input by the user with the input means and the time measured by the measuring means; and delaying means for delaying the start of operation of the memory means to cause the memory means to store the information input by the user with the input means and the time measured by the measuring means at a different time delayed from the predetermined time intervals.

8. A portable device for collecting information about a user according to claim 7; wherein the memory means stores the information input by the user with the input means and the time measured by the measuring means for a plurality of sets of sequentially displayed characters that are displayed in time sequence and for a given duration of time.

9. A portable device for collecting information about a user according to claim 7; further comprising detection means for detecting bodily movements of the user.

10. A portable device for collecting information about a living body according to claim 7; wherein the delaying means includes a switch mounted on the case.

11. A portable device for collecting information about a user, comprising: a case; a timepiece disposed in the case; frontal-lobe-function examining means disposed in the case for executing cognitive ability testing using a display and an input device of the timepiece; and analyzing means for analyzing results of the cognitive faculty tests to determine fluctuations in the user's memory faculty while the user performs different activities.

12. A portable device for collecting information about a user according to claim 11; wherein the analyzing means comprises a computer connectable to the portable device.

* * * * *